United States Patent [19]

Swedlow et al.

[11] Patent Number: 5,392,777
[45] Date of Patent: * Feb. 28, 1995

[54] OXIMETER SENSOR WITH PERFUSION ENHANCING

[75] Inventors: David B. Swedlow, Foster City; Paul D. Mannheimer, Belmont; Jessica A. Warring, Millbrae, all of Calif.

[73] Assignee: Nellcor, Inc., Pleasanton, Calif.

[ * ] Notice: The portion of the term of this patent subsequent to Dec. 7, 2010 has been disclaimed.

[21] Appl. No.: 160,350

[22] Filed: Dec. 1, 1993

Related U.S. Application Data

[63] Continuation of Ser. No. 722,645, Jun. 28, 1991, Pat. No. 5,267,563.

[51] Int. Cl.⁶ .............................................. A61B 5/00
[52] U.S. Cl. ................................ 128/633; 128/664; 128/665
[58] Field of Search .................... 128/633, 664–666; 356/39–41

[56] References Cited

U.S. PATENT DOCUMENTS

| | | |
|---|---|---|
| 3,628,525 | 12/1971 | Polanyi et al. |
| 4,621,643 | 11/1986 | New, Jr. et al. |
| 4,653,498 | 3/1987 | New, Jr. et al. |
| 4,687,481 | 8/1987 | Nuwayser |
| 4,692,462 | 9/1987 | Banerjee |
| 4,747,845 | 5/1988 | Korol |
| 4,764,382 | 8/1988 | Kydonieus et al. |
| 4,825,879 | 2/1989 | Tan et al. ............ 128/633 |
| 4,926,867 | 5/1990 | Kanda et al. ........ 128/633 |
| 4,928,691 | 5/1990 | Nicolson et al. |
| 4,930,506 | 6/1990 | Ullrich ................ 128/633 |
| 5,131,391 | 7/1992 | Sakai et al. .......... 128/633 |
| 5,158,082 | 10/1992 | Jones .................. 128/633 |
| 5,267,563 | 12/1993 | Swedlow et al. .... 128/633 |

OTHER PUBLICATIONS

"Medical Reflection Photometry", Zijlstra & Mook, Van Gorcum's Medical Library nr. 152, The Netherlands, 1962.

Federal Registers, vol. 44, No. 234, Dec. 4, 1979, pp. 69768 and 69830.

"Drug Facts and Comparisons" 1986, pp. 617–619, Facts and Comparisons Div., St. Louis, J. B. Lippincott Company.

Primary Examiner—Lee S. Cohen
Assistant Examiner—Jeffrey R. Jastrzab
Attorney, Agent, or Firm—Townsend and Townsend Khourie and Crew

[57] ABSTRACT

A method and apparatus for a simple pulse oximeter measurement of an area of the body with a small amount of blood vessels by using a counterirritant to profuse the blood and then apply a modern oximeter probe is disclosed. The counterirritant is either applied to the skin immediately before attaching the probe, or, preferably, is contained in an adhesive pad which couples the probe to the skin.

5 Claims, 1 Drawing Sheet

OXIMETER SENSOR WITH PERFUSION ENHANCING

This is a continuation of application Ser. No. 07/722,645, filed Jun. 28, 1991, now U.S. Pat. No. 5,267,563.

BACKGROUND

This invention relates to the noninvasive measurement of a patient's blood characteristics and, in particular, to the use of a pulse oximeter to measure the patient's heart rate and blood oxygen saturation.

The use of pulse oximeters to noninvasively measure a patient's heart rate and arterial blood oxygen saturation is well known. In general terms, noninvasive measurement of arterial blood oxygen saturation typically requires the transcutaneous illumination of a portion of the patient's blood-perfused tissue by light at two or more wavelengths. Changes in the amount of arterial blood in the tissue during a blood pressure pulse change the amount and character of the light detected by the sensor's photodetector. Pulse oximeters identify arterial blood (as opposed to venous blood) from the pulsing component of the optical signal detected by the pulse oximetry sensor. The amounts of light transmitted through the tissue at each wavelength may be compared to calculate to what degree the arterial blood flowing through the tissue is saturated with oxygen. A more detailed discussion of the principles of pulse oximetry may be found in U.S. Pat. No. 4,653,498.

The quality of the pulse oximetry measurement depends in part on the concentration of arterial blood (relative to other tissue structures) in the portion of tissue illuminated by the sensor and in part on the magnitude of the pulsatile changes in the amount of blood in the tissue. For example, while fingers are a preferred sensor site because of their relatively large number and concentration of blood vessels, well-perfused sites such as fingers are not always available. In addition, blood flow to the sensor site may be restricted due to the effects of ambient temperature, systematically acting vasoconstricting drugs in the patient's blood stream, or low patient blood pressure.

The prior art has recognized a need to increase the amount of arterial blood. A device called the "Cyclops" is discussed in W. G. Zijlstra and G. A. Mook, Medical Reflection Photometry, P.50–77(Royal VanGorcum Ltd., Assen, 1962). The Cyclops detects blood by measuring the amount of light reflected from the skin and is preferably placed in the middle of the forehead, thus giving it the name "Cyclops". The skin is first given a treatment of histamine phosphate. This is a counterirritant which has the effect of producing vascular dilation. With the blood vessels dilated, more blood will flow through, providing a larger signal to the sensor.

A voltage is applied to the skin to drive the histamine phosphate into the tissue by a process called histamine iontophoresis. Subsequently, a compression plate is applied to the skin to make it bloodless to enable a base line measurement of the light reflection value. Thereafter, blood is allowed to flow to dilated vessels and measurements are taken of the blood oxygen level.

In more recent years, pulse oximeter devices have been developed which use multiple light wavelengths and sophisticated waveform analysis which allows a pulse waveform to be analyzed at its peaks and valleys, eliminating the need for making a bloodless base line measurement. These devices have attempted to provide a simple, compact sensor which can provide all the necessary preparation and analysis with a single application of the sensor, without the need for the multiple steps of the prior art Cyclops. For example, U.S. Pat. No. 4,926,867 discloses a pulse oximetry sensor that incorporates a heater and a temperature control. That patent states that the application of heat to the patient's skin at the sensor site increases the flow of arterial blood through the capillaries beneath the sensor, thereby increasing the pulse to pulse changes in the optical signal derived by the sensor.

U.S. Pat. No. 4,852,879 discloses another prior art approach to the blood perfusion problem. In that patent, the inventors recognize that the addition of a heater to the sensor increases its complexity and makes it more costly. The inventors therefore added a thermally reflective metal layer to the pulse oximeter sensor in order to retain body heat at the sensor site.

SUMMARY OF THE INVENTION

The present invention provides a method and apparatus for a simple pulse oximeter measurement of an area of the body with a small amount of blood vessels by using a counterirritant to profuse the blood and then apply a modern oximeter probe. The counterirritant is either applied to the skin immediately before attaching the probe, or, preferably, is contained in an adhesive pad which couples the probe to the skin.

The present invention recognizes the ability of the counterirritant to profuse the blood without the need for iontophoresis. In addition, the use of an adhesive pad uniquely allows a single step application of the counterirritant with the attachment of the probe.

The present invention improves over the heating systems of the recent prior art. Since much of the heat in the tissue beneath the patient's skin is provided by the blood flowing through that tissue, passive heat retaining sensor bandages will be useful primarily in low ambient temperature environments. These heat reflectors would do little to improve the sensor's performance if the lack of blood perfusion were due to causes other than cold air surrounding the sensor site.

Mechanical heaters, on the other hand, may be unduly complex and costly. In addition, unregulated sensor heaters are a burn risk. What is needed, therefore, is an easy and inexpensive way to increase blood perfusion at the sensor site.

The method of this invention meets this need. The invention is described more particularly below with reference to the drawings.

DETAILED DESCRIPTION OF THE PREFERRED EMBODIMENT

Figure 1A:
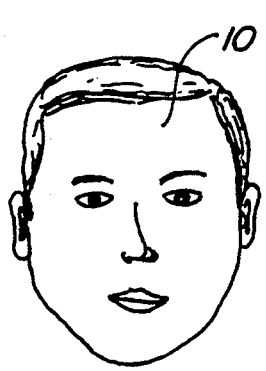
FIGS. 1(a) to 1(c) depict a method for optically measuring a characteristic of a patient's blood according to one embodiment of this invention.
Figure 1B:
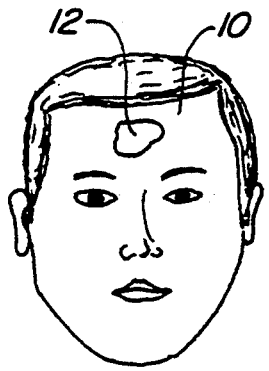
Figure 1C:
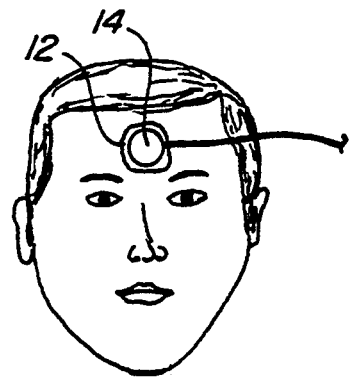

One example of the method of this invention is shown in FIG. 1. As shown in Figs. 1(a) and 1(b), a small amount 12 of a counterirritant, such as a mixture of methyl salicilate and menthol (12% methyl salicilate, 9% menthol) in a cream base is applied to the patient's skin at the chosen sensor site 10. A cream of this type is sold in retail drug stores under the trademark ICY HOT.

After application of the cream, a pulse oximeter sensor 14 is placed on the sensor site, and pulse oximetry measurements are taken in the usual way. In this example, the chosen site 10 is the patient's forehead, and sensor 14 is a surface or transflectance pulse oximetry sensor, such as the NELLCOR RS-10 sensor. The calculation of the oxygen level without the need for a bloodless baseline calibration is done with a pulse oximeter monitor such as that disclosed in U.S. Pat. No. 4,521,643 hereby incorporated herein by reference. Our tests have shown that application of a small amount (on the order of 0.025 ml.) of the methyl salicilate cream to the patient's skin at the chosen sensor site increases the magnitude of the optical pulse detected by the sensor.

It should be understood that other locally acting blood perfusion enhancing substances (such as local skin irritants or vasodilators), other application methods, other sensor sites and other sensor configurations may be used without departing from the scope of this invention. For example, the methyl salicilate cream may be applied to the patient's finger prior to placement of a transmissive finger pulse oximeter sensor.

Figure 2:
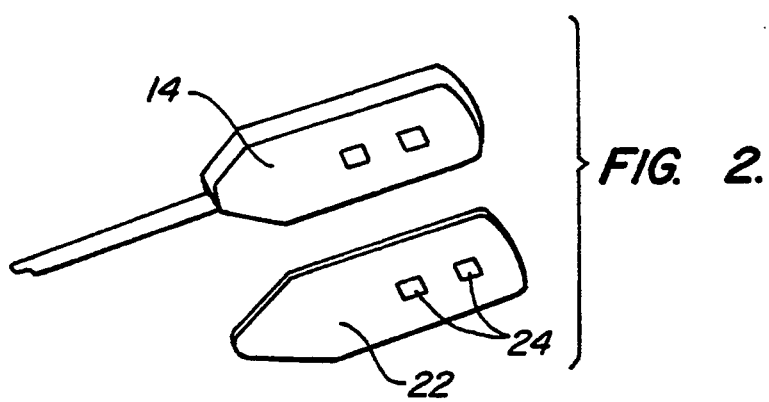
FIG. 2 shows a pulse oximetry sensor and a patch containing a locally acting blood perfusion enhancing substance according to another embodiment of this invention.

As another example, the perfusion-increasing substance can be applied to the sensor site through an adhesive patch, such as the motion-sickness medicine patch marketed by the Alza Corporation. Use of an adhesive patch as the substance delivery device may prolong the perfusion enhancing effect of the substance by continually applying the substance over a period of time. General guidelines for the construction and use of transdermal adhesive patches are set forth in a number of U.S. Pat. Nos. including 4,687,481; 4,692,462; 4,764,382; 4,747,845; and 3,993,073, the disclosures of which are incorporated herein by reference. One possible configuration of a sensor 14 and an adhesive patch 22 containing the perfusion enhancing substance is shown in FIG. 2. Holes 24 in the patch permit transmission and reception of light by the sensor 14.

The substance may also be applied via the adhesive used to attach the sensor to the patient's sensor site. Other variations will be obvious to those skilled in the art.

What is claimed is

1. A method for optically measuring a characteristic of a patient's blood comprising the following steps:
    applying to a predetermined location on the patient's skin a blood perfused tissue altering substance without the use of iontophoresis;
    placing a sensor on the predetermined location of the patient's skin, the sensor comprising a light source and a photodetector;
    transmitting light from the light source into the patient's skin at the predetermined location;
    detecting light with the photodetector at the predetermined location; and
    measuring a characteristic of the patient's blood based on the detected light.

2. The method of claim 1 wherein said substance is a counterirritant.

3. A sensor system comprising:
    an optical sensor;
    an adhesive patch means for attaching the optical sensor to a sensor site on a patient's skin and
    for applying a blood perfused tissue altering substance to the sensor site.

4. The sensor of claim 3 wherein said adhesive patch means has holes for allowing light to pass from said optical sensor.

5. The system of claim 3 wherein said substance is a counterirritant.

* * * * *